(12) United States Patent
Jones et al.

(10) Patent No.: US 8,241,035 B2
(45) Date of Patent: *Aug. 14, 2012

(54) DEVICE HAVING ACTIVATED TEXTURED SURFACES FOR TREATING ORAL TISSUE

(75) Inventors: Jeffrey W. Jones, Robertson, WY (US); Ioana M. Rizoiu, San Clemente, CA (US); Dmitri Boutoussov, Dana Point, CA (US)

(73) Assignee: BIOLASE, Inc., Irvine, CA (US)

( * ) Notice: Subject to any disclaimer, the term of this patent is extended or adjusted under 35 U.S.C. 154(b) by 822 days.

This patent is subject to a terminal disclaimer.

(21) Appl. No.: 11/441,788

(22) Filed: May 25, 2006

(65) Prior Publication Data

US 2007/0009856 A1    Jan. 11, 2007

Related U.S. Application Data

(60) Provisional application No. 60/684,418, filed on May 25, 2005, provisional application No. 60/703,962, filed on Jul. 29, 2005, provisional application No. 60/739,273, filed on Nov. 23, 2005.

(51) Int. Cl.
*A61C 1/00* (2006.01)

(52) U.S. Cl. ........................................... 433/29

(58) Field of Classification Search ............... 433/29, 433/215, 80; 128/861, 62; 15/22.1, 105, 15/167.1

See application file for complete search history.

(56) References Cited

U.S. PATENT DOCUMENTS

| | | |
|---|---|---|
| 407,115 A | 7/1889 | Pratt |
| 2,834,344 A | 5/1958 | Kanai |
| 3,261,978 A | 7/1966 | Brenman |
| 3,478,741 A | 11/1969 | Simor |
| 3,520,297 A | 7/1970 | Bechtold |
| 4,237,574 A * | 12/1980 | Kelly et al. .................. 15/167.2 |
| 4,273,535 A | 6/1981 | Yamamoto et al. |
| 4,502,497 A | 3/1985 | Siahou |
| 4,661,070 A | 4/1987 | Friedman |
| 4,672,706 A | 6/1987 | Hill |
| 4,779,173 A | 10/1988 | Carr et al. |
| 4,877,401 A | 10/1989 | Higuchi et al. |
| 4,890,732 A | 1/1990 | Shackleford |
| 4,952,143 A | 8/1990 | Becker et al. |

(Continued)

FOREIGN PATENT DOCUMENTS

EP    0 406 454    1/1991

(Continued)

OTHER PUBLICATIONS

International Search Report, Feb. 2, 2008, PCT/US06/19630.

(Continued)

*Primary Examiner* — Sunil K Singh
(74) *Attorney, Agent, or Firm* — Stout, Uxa, Buyan & Mullins, LLP

(57) ABSTRACT

Mouthpieces having activated textured surfaces that can be implemented using repetitive movement mechanisms and energy (e.g., electromagnetic radiation) emitting sources are disclosed. The mouthpieces may be used to provide detection, treatment and management of conditions including tooth discoloration and periodontal disease. Implementations can include a low-profile mouthpiece or a mouthpiece covering only front sides of the upper and lower teeth. Other combinations may include full-mouth implementations suitable for simultaneously covering part or all of a patient's upper and lower rows of teeth. The activated textured surfaces may include a surface topography consisting of bristles.

25 Claims, 8 Drawing Sheets

U.S. PATENT DOCUMENTS

| | | | |
|---|---|---|---|
| 4,969,868 A | | 11/1990 | Wang |
| 4,983,381 A | | 1/1991 | Torres Zaragoza |
| 5,003,434 A | | 3/1991 | Gonser et al. |
| 5,030,090 A | | 7/1991 | Maede et al. |
| 5,030,093 A | | 7/1991 | Mitnick |
| 5,032,178 A | | 7/1991 | Cornell |
| 5,055,048 A | | 10/1991 | Vassiliadis et al. |
| 5,094,619 A | | 3/1992 | McLaughlin |
| 5,160,194 A | | 11/1992 | Feldman |
| 5,306,143 A | | 4/1994 | Levy |
| 5,365,624 A | * | 11/1994 | Berns .................. 15/22.1 |
| 5,611,793 A | | 3/1997 | Wilson et al. |
| 5,645,428 A | | 7/1997 | Yarborough |
| 5,658,148 A | | 8/1997 | Neuberger et al. |
| 5,690,913 A | * | 11/1997 | Hsu et al. .................. 424/53 |
| 5,879,159 A | | 3/1999 | Cipolla |
| 6,026,828 A | | 2/2000 | Altshuler |
| 6,089,740 A | | 7/2000 | Forehand et al. |
| 6,202,242 B1 | | 3/2001 | Salmon et al. |
| 6,397,860 B1 | * | 6/2002 | Hill, II .................. 132/309 |
| 6,616,447 B1 | | 9/2003 | Rizoiu et al. |
| 6,616,451 B1 | | 9/2003 | Rizoiu et al. |
| 6,685,471 B1 | | 2/2004 | Kawamura et al. |
| 6,862,771 B1 | | 3/2005 | Muller |
| 2003/0099502 A1 | | 5/2003 | Lai |
| 2003/0232303 A1 | | 12/2003 | Black |
| 2004/0006332 A1 | | 1/2004 | Black |
| 2004/0072122 A1 | | 4/2004 | Hegemann |
| 2004/0091834 A1 | | 5/2004 | Rizoiu et al. |
| 2004/0191729 A1 | * | 9/2004 | Altshuler et al. .............. 433/215 |
| 2004/0193235 A1 | | 9/2004 | Altshuler et al. |
| 2004/0193236 A1 | | 9/2004 | Altshuler et al. |
| 2004/0204745 A1 | | 10/2004 | Altshuler et al. |
| 2004/0210276 A1 | | 10/2004 | Altshuler et al. |
| 2005/0050658 A1 | | 3/2005 | Chan et al. |
| 2005/0050659 A1 | | 3/2005 | Chan et al. |
| 2005/0053895 A1 | | 3/2005 | Pinyayev et al. |
| 2005/0053896 A1 | | 3/2005 | Pinyayev et al. |
| 2005/0053898 A1 | | 3/2005 | Ghosh et al. |
| 2005/0107849 A1 | | 5/2005 | Altshuler et al. |
| 2009/0031515 A1 | | 2/2009 | Rizoiu et al. |
| 2009/0056044 A1 | | 3/2009 | Rizoiu et al. |
| 2009/0271936 A1 | | 11/2009 | Walanski et al. |

FOREIGN PATENT DOCUMENTS

| | | |
|---|---|---|
| JP | 6125812 A | 5/1994 |
| RU | 2234287 C2 | 8/2004 |
| RU | 2239342 C2 | 11/2004 |
| WO | WO/92/06671 | 4/1992 |
| WO | WO/93/09847 | 5/1993 |
| WO | WO/94/09850 A | 5/1994 |
| WO | WO/97/01298 | 1/1997 |
| WO | WO/98/10711 A | 3/1998 |
| WO | 9858595 A1 | 12/1998 |

OTHER PUBLICATIONS

International Search Report, Jun. 11, 2008 PCT/US06/20501.
International Preliminary Examination Report, Mar. 15, 2000, PCT/US98/12836.
International Search Report, Dec. 30, 1998, PCT/US98/12836.
European Search Report, Jul. 15, 2005, EP 98 93 1410.
Supplementary European Search Report from Application No. EP 06760434, dated Sep. 16, 2009.
International Search Report and Written Opinion, PCT/US10/61139, mailed Feb. 18, 2011.
International Search Report and Written Opinion, PCT/US2011/027604, mailed May 12, 2011.

* cited by examiner

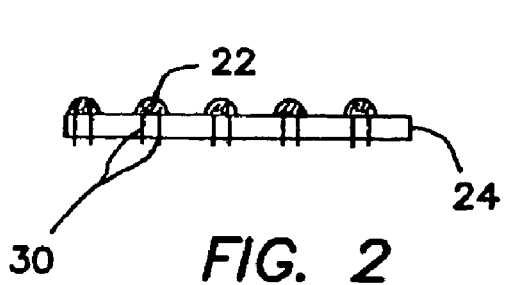
FIG. 2
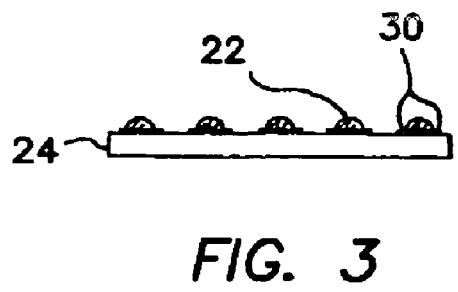
FIG. 3
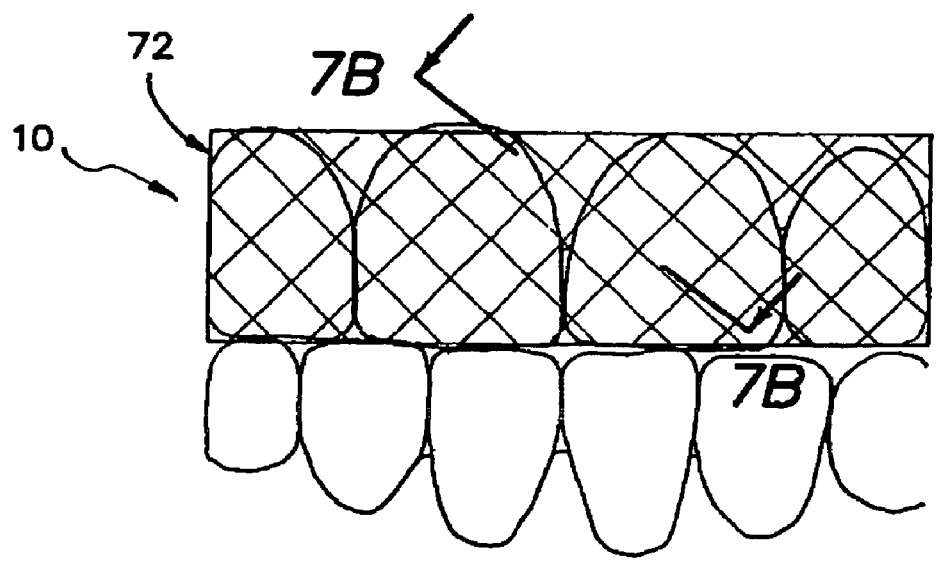
FIG. 7A
FIG. 7B
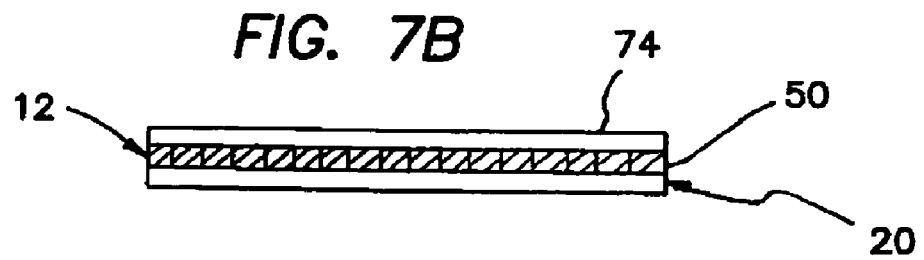

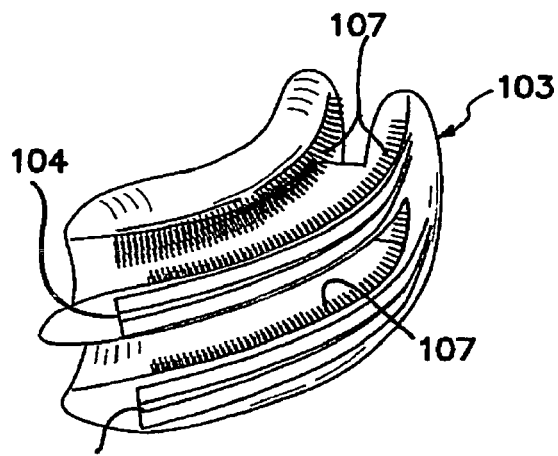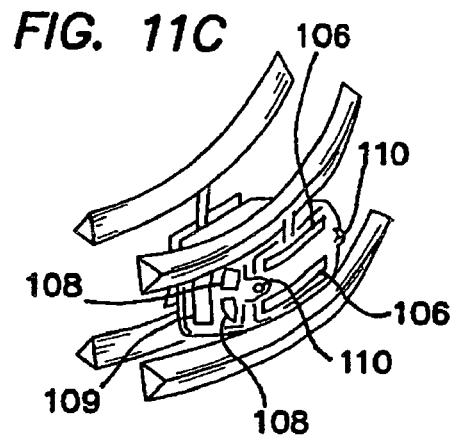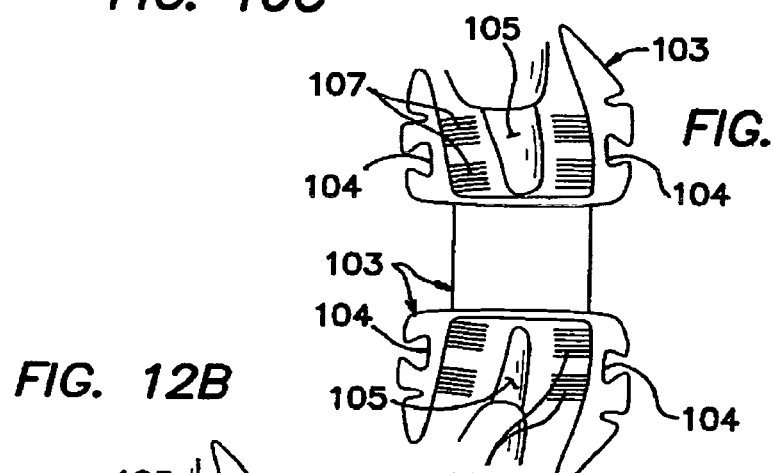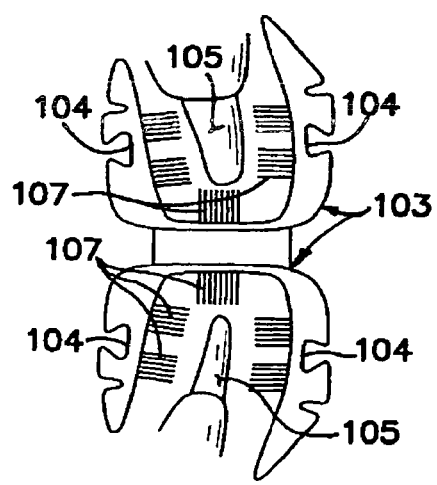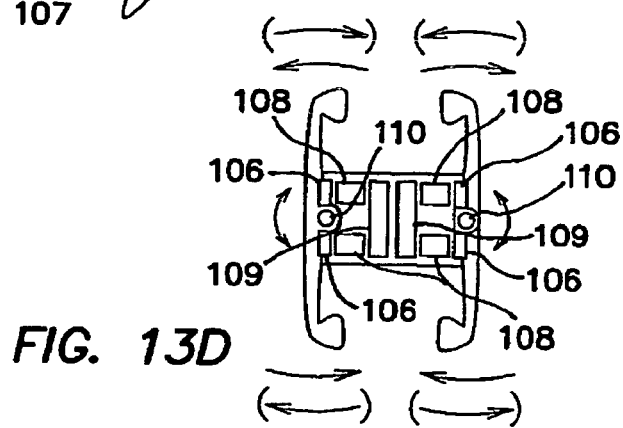

DEVICE HAVING ACTIVATED TEXTURED SURFACES FOR TREATING ORAL TISSUE

CROSS-REFERENCE TO RELATED APPLICATIONS

This application claims the benefit of U.S. Provisional Application No. 60/684,418, filed May 25, 2005 and entitled TISSUE TREATMENT DEVICE HAVING ACTIVATED TEXTURED SURFACES, U.S. Provisional Application No. 60/703,962, filed Jul. 29, 2005 and entitled TISSUE TREATMENT DEVICE HAVING ACTIVATED TEXTURED SURFACES, U.S. Provisional Application No. 60/739,273, filed Nov. 23, 2005 and entitled TISSUE TREATMENT DEVICE HAVING ACTIVATED TEXTURED SURFACES, the entire contents of all which are hereby incorporated by reference.

This application is related to U.S. application Ser. No. 11/074,452, filed Mar. 8, 2005 and entitled RADIATION EMMITTING APPARATUS WITH SPATIALLY CONTROLLABLE OUTPUT ENERGY DISTRIBUTIONS, which is a continuation of U.S. application Ser. No. 10/229,374, filed Aug. 26, 2002 and entitled RADIATION EMMITTING APPARATUS WITH SPATIALLY CONTROLLABLE OUTPUT ENERGY DISTRIBUTIONS, the entire contents of which are hereby incorporated by reference. This application is also related to U.S. Pat. No. 6,616,447, which issued on Sep. 9, 2003 and which claims the benefit of U.S. Provisional Application No. 60/249,015, entitled DEVICE FOR DENTAL CARE AND WHITENING, and filed Nov. 15, 2000, the entire contents of both which are hereby incorporated by reference.

BACKGROUND OF THE INVENTION

Various mouth trays have existed in the prior art, including mouth trays having or used with light-emitting elements for facilitating treatments such as tooth whitening procedures.

SUMMARY OF THE INVENTION

Carriers, such as a mouthpieces or tongue wraps, coupled with activated textured surfaces that can be implemented using one or more of, for example, a repetitive movement mechanism and an energy (e.g., electromagnetic radiation) emitting source, are provided. The carriers may comprise one or more of an oral tray, an oral band or insert, an oral tape or wrap, any known orthodontic structure (e.g., braces), other similar structure, and combinations thereof, and may be used to provide detection, treatment and/or management of various conditions including, for example, tooth discoloration, tissue damage, periodontal disease, tumorous growth, pain, halitosis and bronchitis. One combination may comprise, for example, a low-profile oral mouthpiece or, as another example, a mouthpiece covering only front sides (e.g., frontal in-view surfaces facing the front of the mouth) of the upper and lower teeth. Other combinations may comprise, for example, full-mouth oral trays suitable for simultaneously covering portions, or all, of a patient's upper and lower rows of teeth. The activated textured surface may include a surface topography comprising bristles.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112.

Any feature or combination of features described herein are included within the scope of the present invention provided that the features included in any such combination are not mutually inconsistent as will be apparent from the context, this specification, and the knowledge of one skilled in the art. In addition, any feature or combination of features may be specifically excluded from any embodiment of the present invention. For purposes of summarizing the present invention, certain aspects, advantages and novel features of the present invention are described. Of course, it is to be understood that not necessarily all such aspects, advantages or features will be embodied in any particular implementation of the present invention. Additional advantages and aspects of the present invention are apparent in the following detailed description and claims that follow.

BRIEF DESCRIPTION OF THE DRAWINGS

FIG. 2 is similar to FIG. 1D without the transparent panel, and showing the use of side mounted contacts.

FIG. 3 is similar to FIG. 2 showing surface mounted contacts.

FIG. 7A is a side elevational view of the device of the invention in which the device is an oral band or oral tape disposed on teeth.

FIG. 7B is a sectional view along line 7B-7B of FIG. 7A.

DETAILED DESCRIPTION OF THE INVENTION

Figure 1A:
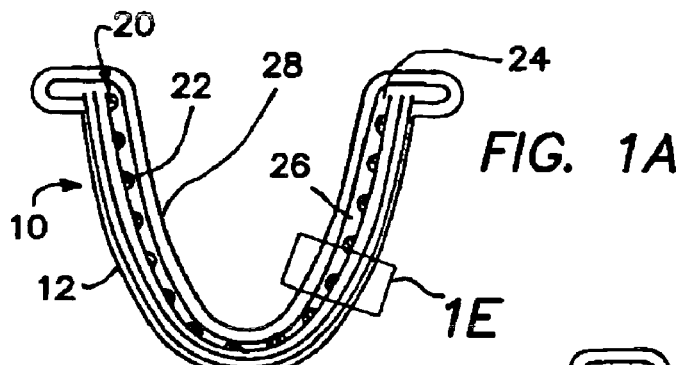
FIG. 1A is a top plan view of the device illustrated in FIG. 1.

Reference will now be made in detail to the presently preferred embodiments of the invention, examples of which are illustrated in the accompanying drawings. Wherever possible, the same or similar reference numbers are used in the drawings and the description to refer to the same or like parts. It should be noted that the drawings are in simplified form and are not to precise scale. In reference to the disclosure herein, for purposes of convenience and clarity only, directional terms, such as, top, bottom, left, right, up, down, over, above, below, beneath, rear, and front, are used with respect to the accompanying drawings. Such directional terms should not be construed to limit the scope of the invention in any manner.

Although the disclosure herein refers to certain illustrated embodiments, it is to be understood that these embodiments are presented by way of example and not by way of limitation. The intent of the following detailed description, although discussing exemplary embodiments, is to be construed to cover all modifications, alternatives, and equivalents of the embodiments as may fall within the spirit and scope of the invention as defined by the claims. It is to be understood and appreciated that the process steps and structures described or incorporated by reference herein do not cover a complete process flow for the implementations described herein. The present invention may be practiced in conjunction with various medical devices that are conventionally used in the art, and only so much of the commonly practiced method steps are included herein as are necessary to provide an understanding of the present invention.

Any feature or combination of features described herein are included within the scope of the present invention provided that the features included in any such combination are not mutually inconsistent as will be apparent from the context, this specification, and the knowledge of one of ordinary skill in the art.

Although the disclosure herein refers to the use of a device having activated textured surfaces for treating tissue (i.e., hard and soft) surfaces of the oral cavity, the device and process of the present invention are not limited to such uses. Devices of the present invention may be used, or modified for use, for any medical purpose that may benefit from the application of automated movement of textured surfaces on or within tissues of the body.

The device of the present invention generally can include a carrier, such as a mouthpiece or tongue wrap, coupled with an activated textured surface that can be implemented using one or more of, for example, a repetitive movement mechanism and an energy (e.g., electromagnetic radiation) source.

The carrier may comprise one or more of an oral tray, an oral band or insert, an oral tape or wrap, any known orthodontic structure (e.g., braces), other similar structure, and combinations thereof. Implementations of the device for treating oral tissue, which can comprise a carrier constructed to be applied in proximity to at least one oral tissue within the mouth, can comprise the device being provided in a package. The carrier may be used to provide detection, treatment and/or management of sundry conditions including, for example, tooth discoloration, tissue damage, periodontal disease, tumorous growth, pain, halitosis, and bronchitis. One combination may comprise, for example, a low-profile oral tray or, as another example, a tray covering only back sides (e.g., frontal out-of-view surfaces facing the back of the mouth) of the lower teeth, wherein, in accordance with one exemplary implementation, the tray includes orthodontic hardware for straightening or otherwise affecting a position of a plurality of teeth. Other combinations may comprise, for example, full-mouth oral trays suitable for simultaneously covering portions (e.g., frontal in-view surfaces facing the front of the mouth), or all, of a patient's upper and lower rows of teeth. In a few exemplary embodiments, the carrier may comprise shapes such as those depicted in FIGS. 1-7B or those shown in FIGS. 8A and 8B.

The activated textured surface may include a surface topography comprising one or more of corrugations, bristles, protuberances, pits, other surfaces known to those skilled in the art to be suitable for facilitating agitation, cleaning or other surface treatments, and combinations thereof. Surface topographies of or analogous to one or more of sponges, fabrics, brushes, steel wool, toothbrushes, other cleaning or wiping surfaces, and combinations thereof, may be implemented using various known materials. For example, surface topographies of household cleaning, wiping, or scrubbing pads comprising, for example, one or more of rayon/polypropylene fabrics or sponges, polyester fabrics and polyester knits may be implemented using the same or different materials. Textured surfaces may comprise, as other examples, silicon or rubber base materials with surface topographies defined by one or more of plastic, silicon, hardened durometer rubber or stainless steel protuberances or indentations.

The repetitive movement mechanism may comprise one or more of a surface disrupting mechanism, a mechanical movement mechanism, other implementations for activating (e.g., facilitating repetitive movement of) the textured surface, and combinations thereof. In certain embodiments, the textured surface can be activated using, for example, an element for imparting movement forces to the textured surface. The element may facilitate oscillating or acoustics (e.g., ultrasonic) motion by way of, for example, motorized or vibrating devices. Motorized devices may comprise, for example, electromechanical devices powered by batteries or power chords, and vibrating devices may comprise, for example, water-powered or piezoelectric implementations formed on or within the carrier. In other embodiments, movement from an external source, such as a hand of a user, a tool, or other implementations that can be coupled (e.g., attached or placed into contact) with the carrier to facilitate (e.g., transfer) movement of or to the textured surface, may be implemented.

An energy (e.g., electromagnetic radiation) source may be used, solely or in combination with a movement mechanism, to activate the textured surface. In certain implementations, the energy source can comprise at least one light source and can be disposed on the carrier or routed to the carrier via, for example, a fiber optic. In typical embodiments, the light source can be configured to emit one or more of coherent or non-coherent light at a single or multiple wavelengths (e.g., visible, infrared, etc.), and can comprise one or more of a light emitting diode, an optical fiber panel, an electrochemiluminescent material, an optical fiber bundle, and combinations thereof.

The energy source may comprise any known implementation for emitting treatment doses of energy (e.g., electromagnetic energy) toward one or more of the textured surface and the tissue surface. According to one embodiment, the energy may be delivered, in whole or in part, as magnetism (e.g., from magnets within, or electrically activated within, the carrier) for implementing, for example, magnetic therapy. In certain embodiments, the energy may comprise one or more of a, current, voltage, acoustics (e.g., sonic) or vibrational energy (e.g., using vibrations, ultrasound or other acoustic means), electromagnetic as discussed above, reactionary energy (e.g., energy resulting from chemical reactions).

As used herein, the term "treatment doses" is intended to refer to quantities and concentrations of electromagnetic energy that are sufficient to effectuate desired chemical (e.g., enhancing a reaction time) or other (e.g., ablation) reactions on the textured surface or tissue surface and/or to cause one or more therapeutic or other intended effects (e.g., greater circulation or pain reduction) on or in the tissue of the tissue surface. In certain implementations, low-level light therapy (LLLT) may be beneficially applied to tissues using (e.g., via light transmitted from) the carrier. Treatment power densities may be relatively low, being similar, for example, to power densities used in treatments of, e.g., tennis elbow, temporomandibular joint (TMJ), or tendonitis, and in representative embodiments having characteristics less than the following: a power density at the surface of the tissue being treated of about 1.47 W/cm$^2$, a power density within the tissue of about 0.39 W/cm$^2$, a dose of energy of about 23.6 J/cm$^2$ (for a 60 second laser exposure), and/or an energy of about 9 J within and about 33.5 J at the surface of the tissue being treated. In an embodiment wherein the carrier comprises an orthodontic structure (e.g., braces), an electromagnetic radiation source may be incorporated to implement LLLT and reduce pain experienced by the patient from the orthodontic structure. The LLLT may originate from an electromagnetic radiation source disposed on or within the carrier as described herein and/or disposed separate and apart from the carrier, and may be implemented continuously or at predetermined periods of time (e.g., at times when the orthodontic structure is tightened) for predetermined durations.

According to embodiments wherein a dentifrice is used in combination with the electromagnetic radiation source, the dentifrice may comprise, for example, a reactive agent (e.g., a peroxy compound), and a wavelength of the electromagnetic radiation source may be selected to correspond to that agent in order to effectuate a desired reaction or result (e.g., enhanced tooth whitening). In one embodiment, the electromagnetic radiation source is selected to emit green light, which has been found by the present inventors to potentially interact more favorably or stronger than other colors, such as red, with a hydrogen peroxide based dentifrice.

In modified embodiments, part or all of the carrier (e.g., mouthpiece) can comprise a light-emitting compound such as an electrochemiluminescent material or other "glow-in-the-dark" type material, which may be implanted into the carrier in various locations and formations or which may be integrally formed with part or all of a material of the carrier. Additionally, or alternatively, part or all of the carrier may be formed of a transparent material.

The electromagnetic radiation may or may not be combined with a dentifrice, such as a paste, gel, cream, or powder, and may facilitate oral treatments including one or more of, for example cleaning or reducing bacteria on or in hard or soft tissue, promoting blood circulation or healing of tissue, inhibiting caries, whitening teeth, preventing tooth demineralization, etching tooth enamel or dentin, and other similar methods.

As used herein, electromagnetic radiation or electromagnetic energy refers to monochromatic or polychromatic radiation or energy. In a preferred embodiment, electromagnetic radiation refers to light radiation or light energy. The electromagnetic radiation can be delivered, for example, in treatment doses to, for example, increases a therapeutic or other effect on the tissue. In one example, a reaction rate of photosensitive agents, such as teeth whitening agents, can be enhanced. In accordance with one aspect of the present invention, the electromagnetic radiation may be substantially free from ultraviolet radiation. In addition, the wavelengths of the electromagnetic radiation may be provided between approximately 300 and 990 nanometers, or up to about 1 micron. Suitable means that may be used to generate the electromagnetic radiation, in addition to those mentioned, may include, for example, a semiconductor laser that generates monochromatic electromagnetic radiation or a light emitting diode (LED) that emits polychromatic, or alternatively, monochromatic, electromagnetic radiation. A non-limiting example of a laser source may comprise a Nd:YAG laser, although various other lasers having various wavelengths in the UV, visible and IR spectrum, for example, may be implemented individually or in combinations.

The movement mechanism may be implemented with (e.g., simultaneously or intermittently) or without the electromagnetic radiation and/or dentifrice, and may enhance or alter any of the actions or effects described herein and/or may provide other actions or effects to the tissue being treated. Actions or effects that may be imparted can include, as a few examples, one or more of (a) cleaning or massaging of soft tissue such as the gums or tongue, (b) promotion of cleaning (e.g., removal of bacteria, tarter, calculus or plaque) or whitening of hard tissues, (c) surface agitation, (d) an enhanced reactive effect (e.g., enhanced oxidation of a peroxide cleaning agent on teeth), (e) enhance circulation or other properties of tissue, (f) render tissue more receptive to other treatments (such as may occur with low level light therapy (LLLP), (g) enhance an absorption of tissues to topographical additives (e.g., anesthetics or medicines), (h) enhanced halitosis detection (e.g., greater air circulation which may aid in speed or precision of halitosis detection or treatment) or treatment (e.g., augmented cleaning effects).

In the context of promoting cleaning of hard tissues, such as teeth, through, for example, the removal of bacteria, tarter, calculus and/or plaque, a carrier may be provided in the form of a mouthpiece having activated (e.g., moving and/or energized) textured surfaces (e.g., bristles) for automatically cleaning (e.g., brushing) a user's teeth. Upon insertion and/or activation of the mouthpiece, either at a home or in a clinic, a user's teeth can be brushed and/or cleaned alone or in conjunction with, for example, a tooth-whitening procedure or implement as described herein.

One embodiment can comprise a vibrating mouthpiece or mouth tray that brushes the user's teeth with little, and in certain implementations, substantially no, effort on the part of the user following insertion and activation of the mouthpiece. Such energized teeth-cleaning mouthpieces may provide advantages, including the feature that according to certain implementations once placed in the mouth, the user does not have to move the mouthpiece around like a manual tooth brush; in fact, even a conventional power brush will typically require manual motion and moving around the mouth on the part of the user during the entire brushing procedure.

The energized mouthpiece of the present invention, thus, may result in greater compliance with patients, since, for example, according to certain exemplary implementations, once placed it the mouth, the device can be left there until, for example, it beeps, and/or shuts off.

Furthermore, any electronic input/output device or functionality described herein may be operable with the energized mouthpiece so that, for example, a memo pad or to-do list may be played to the user while he or she is operating the energized mouthpiece in lieu of brushing wherein the user has both hands free and available for other tasks during the cleaning procedure. A tooth-brushing and/or cleaning mouthpiece as described herein may be implemented by a user as an alternative to, or as an addition to, use of a toothbrush by the user to clean his or her teeth.

In addition to, or as an alternative to, bristles, the mouthpiece may comprise any other textured surface and/or energy source as described herein, in any permutation or combination, such as, for example, vibrational or acoustics (e.g., sonic) based cleaning structures and functionalities, or other motion or energy structures and functionalities, provided on or within or in conjunction with the mouthpiece. Dentifrices for use with the energized mouthpiece may comprise gels or pastes, such as are known to those skilled in the art and as are described herein. Moreover, circulating, or moving fluid, may be provided or facilitated within the mouthpiece for promoting or promoting one or more different effects, such as cleaning, whitening, rinsing, and the like.

The device of the invention may also be provided with a circuit, and/or microprocessor (e.g., computer chip), for controlling, for example, one or more of any characteristic or functionality of the electromagnetic radiation source and/or the movement mechanism in accordance with, for example, desired or predetermined procedural steps or patient protocols or needs. Moreover, the circuit may be configured to control, for example, one or more of any characteristic of an electronic input/output device and a detector, either or both of which may be used in combination with (e.g., coupled to) the carrier.

The electronic input/output device may comprise, for example, one or more of an audio playback and/or recording system and a video playback and/or recording system. In certain implementations, the detector may comprise one or more of an impedance, current, or microvoltage detector, a magnetic detector, a sonar (e.g., using vibration ultrasound, or other acoustic energy) detector, an optical (e.g., using light scattering) detector, a visualization device (e.g., a single frame or video camera), and a gas detector. The detector can be used for detecting tissue conditions, such as, for example, in the case of oral applications, dental carries, periodontal disease, bronchitis, tumorous growth, or halitosis.

According to an aspect of the present invention, a detector may be used in combination with the carrier to detect conditions of tissues contacted by or disposed in a vicinity (e.g., a relatively close proximity) of the carrier. The detector may or may not be operatively coupled to (e.g., in physical or data communication with) the carrier. In exemplary embodiments, the detector may be coupled to or disposed on the electromagnetic radiation source (e.g., at or near an output end of a laser). In accordance with certain implementations, the detector may be disposed within or on an exposed surface of the carrier. In exemplary embodiments, the detector may be molded within the carrier. For instance, a detector for discerning at least one condition of a tissue (e.g., tooth or gingiva), by for example detecting one or more of a resistance/current/microvoltage, magnetic, acoustics (e.g., sonic), and optical response of the tissue, may be embedded within the carrier. In certain embodiments, the detector may be operatively coupled to the carrier but disposed neither within nor on a surface of the carrier. For example, the detector may employ one or more of visualization (e.g., an integral or stand-alone video camera), impedance, current or potential, magnetism, sonar and optical implementations to facilitate detection, discernment or collection of information (e.g., visual information in the case of a camera) regarding tissue conditions or tissue locations, such as, for example, plaque, calculus (tartar) or carries on a target (e.g., user's teeth or gingival).

According to alternative embodiments, the detector may comprise a gas detector, implemented alone or in combination with any of the preceding detectors, structures and implementations, and configured to facilitate detection, discernment or collection of airborne-agent information (e.g., by sampling air near a target tissue for the presence of predetermined items or chemicals as known in the art) regarding tissue conditions or tissue locations, such as, for example, halitosis on a user's teeth, after which, for example, a carrier may be loaded with a dentifrice (e.g., comprising an antiseptic or cleaning agent) in a manor similar to that previously discussed in order to address the condition.

Architectures and signal processing protocols for implementing impedance, current, potential, magnetic, acoustics (e.g., sonic), optical, and airborne-agent data and signals to discern properties (e.g., the presence of treatable conditions) of targets (e.g., tissues) are known to those skilled in the art and are incorporated herein by reference. In one embodiment, the visualization device can comprise an intraoral video camera such as that manufactured by RFSYSTEMlab of Nagano, Japan and described at www.rfsystemlab.com. The intraoral video camera may be constructed with one or more light sources having wavelengths and associated circuitry designed to elucidate (e.g., visually differentiate) one or more tissue conditions. Light sources having one or a plurality of wavelengths, when directed on tissue within an oral cavity alone or in combination with a coloring agent applied to the tissue, may operate to facilitate an identification of a tissue condition, such as caries.

In connection with (e.g., following a detection of) a treatable condition (e.g., a presence of plaque, calculus or carries) on or in a vicinity of a target (e.g., tissue), a treatment implementation may be configured (e.g., equipped, activated or programmed) on, within, or in connection/communication with the carrier, or apart from the carrier. The treatment implementation may comprise, for example, an implementation for application to the target and may comprise one or more of an activated textured surface, a chemical (e.g., an organic enzyme), fluid, acoustics (e.g., ultrasound), air-abrasion, and laser energy. For instance, in the case of a treatment condition comprising a presence of plaque on a tooth, the treatment implementation may comprise an oscillating and/or vibrating textured (e.g., bristled) surface, a chemical plaque remover within a dentifrice and/or a plaque-remover implementation utilizing one or more of acoustics (e.g., ultrasound), air-abrasion, or laser energy. The treatment implementation may be configured, in whole or in part, at a time of manufacture or assembly of the carrier, or otherwise before detection of the treatable condition, and/or at a time after detection of the treatable condition. Moreover, the configuring may be based upon one or more predetermined criteria and/or based upon information corresponding to the detection of the treatable condition. Furthermore, the treatment implementation may be configured to be applied relatively evenly over the target, or may be configured to be applied in such a manor as to provide greater concentrations of treatment (e.g., plaque-removal action) in certain locations such as, for example, locations detected (e.g., visually observed) or otherwise discerned or determined to contain the treatable condition. In other embodiments, the treatment implementation may comprise one or more of (a) any of preceding treatment implementations, and (b) one or more of a textured surface (which may or may not be part of a carrier and which can be activated), chemical, fluid, acoustics (e.g., ultrasound), air-abrasion, and laser energy that can be applied, in whole or in part, to the target using (at least in part) structures or methods other than the carrier, such as via a hand of a user. Thus, the treatment implementation may be applied to the target using one or more of a carrier and an implementation other than the carrier such as by way of a hand of a user.

According to exemplary embodiments, a detector (e.g., an optical detector) of the carrier may discern a tissue condition (e.g., a cut on a user's tongue), after which a treatment (e.g., LLLT) may be directed onto the tissue as previously described. The treatment may be preceded by one or more of (a) a prompt by the electronic input/output device (e.g., via a speaker and/or display disposed on a carrier charging and/or disinfecting station, the carrier, a carrier component (e.g., an electronic input/output device in communication with the carrier), or a stand-alone component (e.g., a visualization device separate from the carrier)), and (b) a confirmation input by the user. Alternatively, the treatment may be initiated (e.g., automatically) without any prompt and/or user input.

In other embodiments, following detection, discernment or collection of information regarding conditions or locations of a tissue area of interest, iterative processes may be used to treat the tissue area of interest. For example, location information of a tissue condition may be collected and communicated to the user via the input/output device, followed by the performance of treatments as discussed above, followed by one or more repetitions of the preceding collection, communication, and treatment steps. In certain embodiments, following detection, discernment or collection of information regarding conditions or locations of a tissue area of interest, iterative processes may be used to facilitate further detection, discernment or collection of information regarding the conditions or locations of the tissue area of interest. For example, in a simple implementation, a speaker as described above may issue an audible indication (e.g., beep) when a detector is passed over an area likely to contain a treatable condition, thereby signaling such information to the user and/or signaling to the user that additional detection of the area may be warranted. According to an instance wherein the detector implements one or more of impedance, current, potential, magnetic, acoustic (e.g., sonic), light, visual and gas detection and comprises a wand movable by a hand of a user over oral tissue surfaces, the audible indication may signal to the user that additional detection of the area may be warranted in which case the user may move the wand back to a vicinity where the wand was positioned when the audible indication was issued. In certain embodiments, another audible indication may be issued when the wand is positioned back over the area and/or to signal, once again, to the user that additional detection of the area may be warranted in which case the user may again move the wand back over a vicinity where the wand was positioned when the most recent audible indication was issued.

According to one aspect of the present invention, the electronic input/output device can be configured to provide an indication (e.g., an audible or visual text message or an alarm) that a treatable condition should be brought to the attention of a professional (e.g., a dentist), such as in the case of detection of an advanced carries, periodontal disease, halitosis, or tumorous condition. For example, a scale of threshold levels may be programmed into the electronic input/output device for providing guidance (e.g., via audible or visual tones and/or worded messages) to the user on whether a detected treatable condition may or should be treated by the user at home and/or whether the condition should be brought to the attention of a professional.

According to other implementations, the electronic input/output device may comprise additional functionality and a user interface (e.g., one or more of a speaker, display and keys) for accessing such functionality, disposed on one or more of a carrier charging and/or disinfecting station, the carrier, a carrier component (e.g., an electronic input/output device in communication with the carrier), or a stand-alone component (e.g., an electronic input/output device separate from the carrier).

In embodiments utilizing a display (e.g., as part of a carrier charging and/or disinfecting station), the display may be part of or further comprise (e.g., be interchangeable with) a makeup mirror. For example, a 2-sided rotatable panel may comprise a makeup mirror on a first side and the display on a second side. In embodiments utilizing a speaker and/or a display (e.g., as part of a carrier charging and/or disinfecting station), the display may further or alternatively comprise a telephone and/or videophone functionality.

Other embodiments utilizing a speaker and/or a display (e.g., as part of a carrier charging and/or disinfecting station) may be programmed to indicate user information such as a prerecorded voice segment or photo of a user. In embodiments comprising multiple implements (e.g., carriers), the speaker and/or a display may be programmed to indicate a unique prerecorded voice segment, text message, or photo (e.g., captured with a visualization device) of the user who owns the implement currently removed from the device (e.g., carrier charging and/or disinfecting station). Thus, the voice segment, text message, or photo generated by the speaker or display upon removal by a user of his or her implement can provide a verification that the removed implement does indeed belong to the user.

The additional functionality may comprise an ability to play audio and/or visual information, such as vocabulary or foreign language lessons, music, news, or other prerecorded or real-time content.

In certain embodiments, content may be recorded into the electronic input/output device by the user (e.g., in the form of a memo recorded by the user the preceding evening), and in other implementations playback of the content may be performed according to a duration set by a user-defined timer. For example, in one instance language lessons may be played by the device for a predetermined or user-selected period (e.g., 2 minutes) with each use of the device, whereby the user may endeavor to perform an oral procedure (e.g., wear the carrier, or perform brushing or flossing) for the playback period (e.g., 2 minutes).

The electronic input/output device may be configured to interface (e.g., via wireless, USB, RJ11, RJ45, and other ports) with other computer components, such as personal digital assistants (PDAs), personal computers, handheld and other portable media playback devices, using communication protocols known to those skilled in the art, such as Internet, Ethernet, BlueTooth®, etc. Typical embodiments may comprise, for example, MP3 playing capabilities, email applications and calendar applications. Data concerning any of the above-discussed processes thus may by electronically transferred (e.g., via email) to and from the electronic input/output device. For instance, upon a determination that a treatable condition should be brought to the attention of a professional (e.g., a dentist), such as in the case of detection of an advanced carries or halitosis condition, the electronic input/output device can either automatically or under user control forward relevant information to the professional.

Figure 1B:
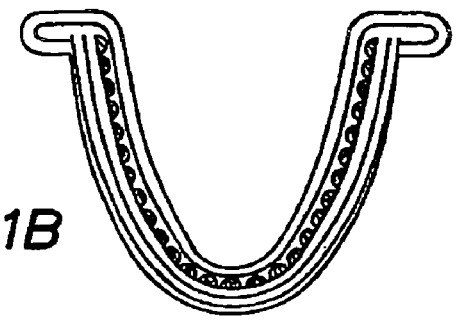
FIG. 1B is a top plan view of the device illustrated in FIG. 1, showing light emitting diodes spaced relatively close together.
Figure 1C:
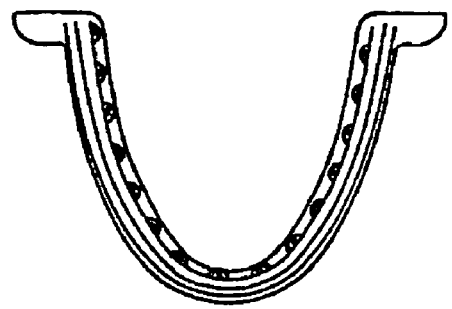
FIG. 1C is a top plan view of the device illustrated in FIG. 1 without a transparent panel covering light emitting diodes.
Figure 1D:
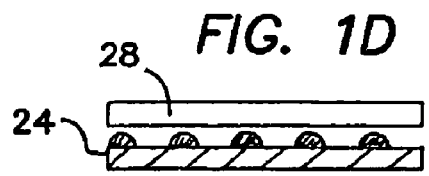
FIG. 1D is a portion of a top plan view of the device illustrated in FIG. 1 showing a transparent panel, light emitting diodes, and a light source panel.
Figure 1F:
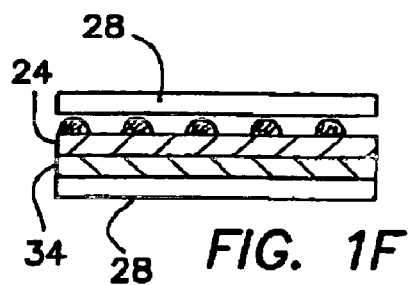
FIG. 1F is similar to FIG. 1E but showing two transparent panels, light emitting diodes, a light source panel, and a reflective panel.
Figure 1E:
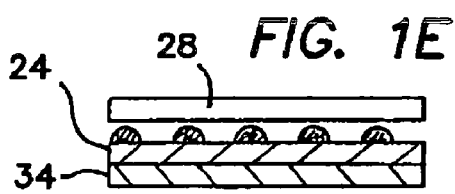
FIG. 1E is a portion along box 1E of FIG. 1A showing a transparent panel, light emitting diodes, a light source panel, and a reflective panel.
Figure 1G:
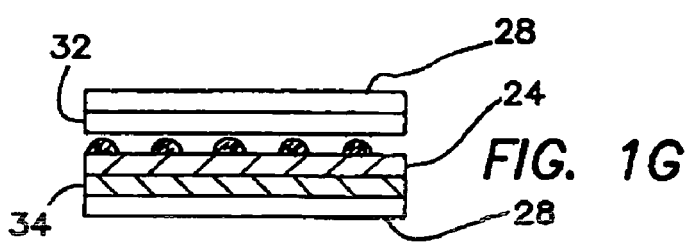
FIG. 1G is similar to FIG. 1F showing a diffuser panel disposed between one transparent panel and the light emitting diodes.
Figure 1:
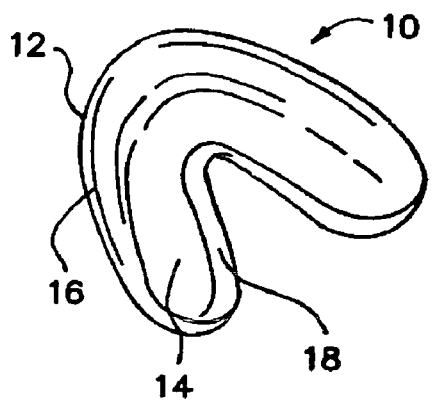
FIG. 1 is a perspective view of an oral device in accordance with the present invention.

Referring more particularly to the illustrated embodiments, FIG. 1 provides a perspective view of a carrier having any of the structures and functionalities as described above, and illustrated in the context of an oral device 10. As illustrated in FIG. 1, oral device 10 comprises an oral tray 12 configured to fit over a person's teeth. For example, oral tray 12, as shown, may fit over a person's upper teeth. Oral tray 12 may be generic or custom designed. The oral tray will fit within a person's mouth, and may cover all of the upper or lower teeth or a portion thereof. In typical embodiments, one oral tray may fit over both the upper and lower teeth, such as a mouth guard typically worn by athletes. In the illustrated embodiment, oral tray 12 includes a tooth bed 14 positioned between an outer sidewall 16 and an inner sidewall 18. Teeth are intended to be placed into tooth bed 14. Outer sidewall 16 will accordingly be disposed between the outer surface of the teeth and a subject's cheeks, and inner sidewall 18 will be disposed between the inner surface of the subject's teeth and the mouth cavity.

The carriers (e.g., oral trays) of the present invention may be manufactured from any suitable material including rubbers and plastics, such as polyethylenes, polypropylenes, and ethyl vinyl acetates. The carriers may be manufactured using, for example, conventional methods used in the manufacture of dental trays. For example, a custom oral tray may be formed by making an impression of a subject's teeth, and may be vacuum or thermoformed over the impression. As shown in FIG. 1A, oral tray 12 can includes an electromagnetic radiation source 20, such as plurality of LEDs 22. LEDs 22 are perimetrically disposed along the interior of the outer sidewall of the oral tray so that energy emitted from the LEDs will be emitted toward the outer surface of a subject's teeth. In the illustrated embodiment, LEDs 22 are attached to light source panel 24. Thus, LEDs 22 can be provided as a strip or array of LEDs embedded, molded, mounted, potted, or otherwise bonded on or within the carrier (e.g., tray). The LED array may include side-mounted LEDs (FIG. 2), surface-mounted LEDs (FIG. 3), or a combination of surface- and side-mounted LEDs. An example of one suitable LED is the publicly available 1005 Series of LEDs from Marktech Optoelectronics (Latham, N.Y., USA).

Although LEDs are illustrated as the electromagnetic radiation source in FIGS. 1-3, other electromagnetic radiation sources may also be used with any of the carriers described herein. Examples of other electromagnetic radiation sources include, but are not limited to one or more of, heat emitting elements, LEDs, lasers or laser diodes, arc lamps, incandescent lamps, halogen lamps, neon lamps, and fluorescent sources. The electromagnetic radiation sources may emit electromagnetic radiation from, for example, ultraviolet to visible to infra-red light. In one embodiment, infra-red spectral energy may be implemented.

LEDs 22 may be covered by a relatively clear or transparent material. The transparent material may be provided as a transparent panel 28 disposed between LEDs 22 and the outer surface of the teeth, as shown in FIG. 1A. However, the transparent material may also be the surface of the oral tray, and not comprise a separate transparent panel, as shown in FIG. 1C. The transparent material can be flexible and moldable so that the panel may conform to the curvatures of a person's mouth. The transparent material can be constructed to emit most of the light from the electromagnetic radiation source to the teeth surface. One example of a suitable transparent materials is moldable, flexible plastic. Transparent panel 28 may be molded, embedded, or attached to the oral tray over light source panel 24. Transparent panel 28 may also protect the LEDs from damage. In addition, a clear resin 26 may be provided between transparent panel 28 and LEDs 22 to provide additional support and protection.

The light sources, such as LEDs 22, may be provided at predetermined distances, for example, one LED per tooth, or may be provided relatively close together, such as illustrated in FIG. 1B. The particular spacings of LEDs 22 can be determined and chosen to optimize the desired treatment (e.g., whitening or cleaning) to be provided by the carrier and/or electromagnetic radiation emitted from the LEDs.

FIG. 1D depicts a portion of a carrier (e.g., oral tray 22) in which the carrier includes a light source panel 24 covered by a transparent panel 28. The effectiveness and efficiency of the emitted electromagnetic radiation may be enhanced by adding a reflector, such as reflective panel 34, positioned against the non-illuminated side of light source panel 24 (e.g., FIGS. 1E to 1G). Any suitable reflector may be used including mirrors and foils. The reflector can be made of a material that causes most, if not all, of the light to be reflected back toward the tooth surface. FIG. 1F shows a portion of a carrier having one transparent panel 28 over light source panel 24, and another transparent panel 28 positioned under reflective panel 34. This additional transparent panel may provide additional protection and structure to the light source panel. In FIG. 1G, a diffuser panel 32 is shown disposed between the light emitting side of light source panel 24 and transparent panel 28. Diffuser panel 32 can acts to diffuse the light and provide a more uniform emission of light toward the tooth surface. In addition, diffuser panel 32 may be a polarizer causing a separation of wavelengths of light, especially in devices employing polychromatic light sources.

Figure 4B:
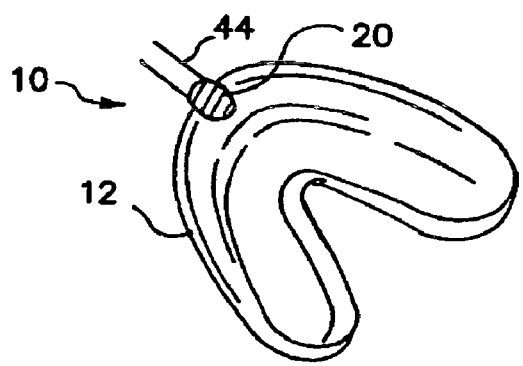
FIG. 4B is similar to FIG. 4A illustrating an embodiment of the device of the invention in which the electromagnetic radiation source is externally located.
Figure 4A:
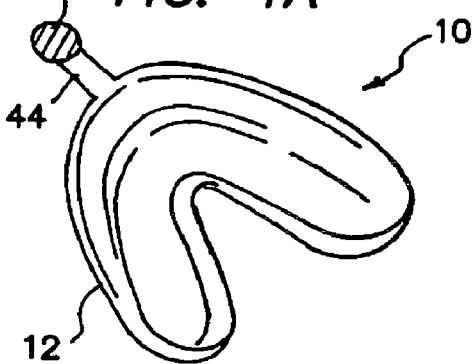
FIG. 4A is similar to FIG. 1 depicting a perspective view of the device of the invention having a fiber optic bundle and an internal electromagnetic radiation source.

As shown in FIG. 2, when side-mounted LEDs are utilized, contacts 30 can extend into light source panel 24. When surface-mounted LEDs are utilized (FIG. 3), contacts 30 can be provided on the surface of light source panel 24. FIG. 4A illustrates oral device 10, such as an oral tray 12, which includes electromagnetic radiation source 20. In the illustrated embodiment, electromagnetic radiation source 20 is internally disposed within oral tray 12. The illustrated embodiment also includes an optical fiber bundle 44 extending into electromagnetic radiation source 20. FIG. 4B illustrates an oral device 10 similar to the oral device of FIG. 4A, except that the electromagnetic radiation source is externally positioned with respect to oral tray 12. Accordingly, optical fiber bundle 44 is disposed between electromagnetic radiation source 20 and oral tray 12. Optical fiber bundle 44 acts to direct light from an energy source to one or more optical fibers.

The oral devices of FIGS. 4A and 4B utilize a light source panel 24 which comprises one or more layers of optical fibers 42 (FIGS. 4C and 4D) or fiber optic pipes. The optical fibers may be woven together. Multiple layers may provide more efficient use of the energy from the electromagnetic radiation source, and may enhance the brightness and uniformity of the light emitted from the light source panel to the target tissue area (e.g., the dentifrice and teeth). The panel of woven optical fibers may be molded or embedded in the oral tray. In another example, light may be emitted from a single side of the panel with a relatively high intensity, and a reflective panel may be provided attached to the outer layer of woven optical fibers. Similarly to the embodiment of FIG. 1, a diffuser panel may be provided to increase the uniformity of the light on the tooth surface. One example of a suitable optical fiber panel is the Lumitex® panel (Lumitex, Inc. Strongsville, Ohio, USA), as disclosed in U.S. Pat. No. 5,613,751, entitled LIGHT EMITTING PANEL ASSEMBLIES, the contents of which are hereby incorporated by reference.

Figure 4C:
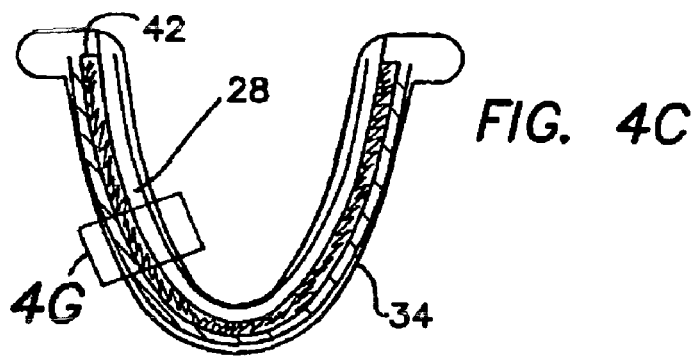
FIG. 4C is a top plan view of the device of FIG. 4A depicting a transparent panel, a diffuser, an optical fiber panel, and a reflective panel.
Figure 4D:
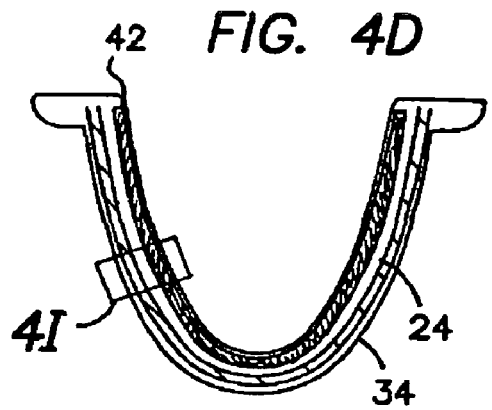
FIG. 4D is similar to FIG. 4C but depicting a transparent panel, an optical fiber panel, a light source panel and a reflective panel.
Figure 4E:
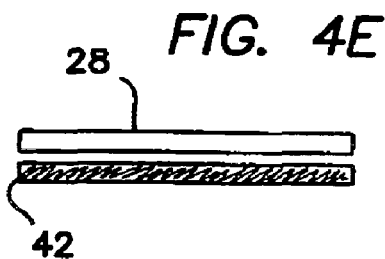
FIG. 4E is a portion of a top plan view of the device of the invention depicting a transparent panel and an optical fiber panel.
Figure 4F:
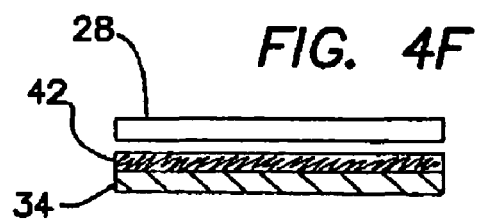
FIG. 4F is a portion of a top plan view of the device of the invention depicting a transparent panel, an optical fiber panel, and a reflective panel.
Figure 4G:
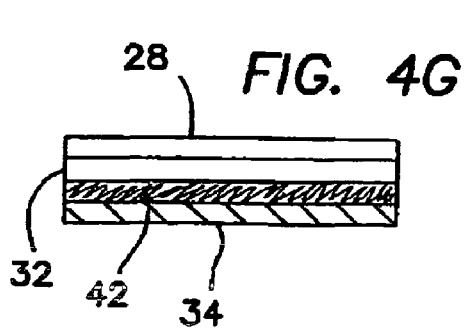
FIG. 4G is a portion along the box 4G of FIG. 4C depicting a transparent panel, a diffuser panel, an optical fiber panel, and a reflective panel.
Figure 4H:
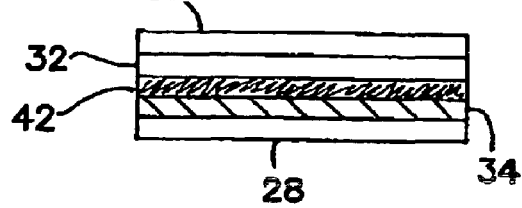
FIG. 4H is a portion of a top plan view of the device of the invention depicting two transparent panels, a diffuser panel, an optical fiber panel, and a reflective panel.
Figure 4I:
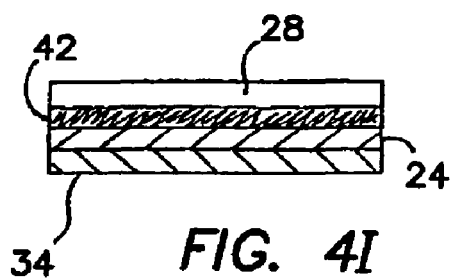
FIG. 4I is a portion along the box 4I of FIG. 4D depicting a transparent panel, an optical fiber panel, a light source panel, and a reflective panel.

FIG. 4E illustrates one device of the invention in which an optical fiber panel 42 is covered by transparent panel 28. FIG. 4F shows a similar device, but one that includes reflective panel 34. FIG. 4G shows a portion along box 4G of FIG. 4C in which diffuser panel 32 is disposed between transparent panel 28, and optical fiber panel 42. FIG. 4H is similar to FIG. 4G showing an additional transparent panel 28 below reflective panel 34. FIG. 4I is taken along the box 4I of FIG. 4D, illustrating a light source panel 24 below optical fiber panel 28.

Figure 8A:
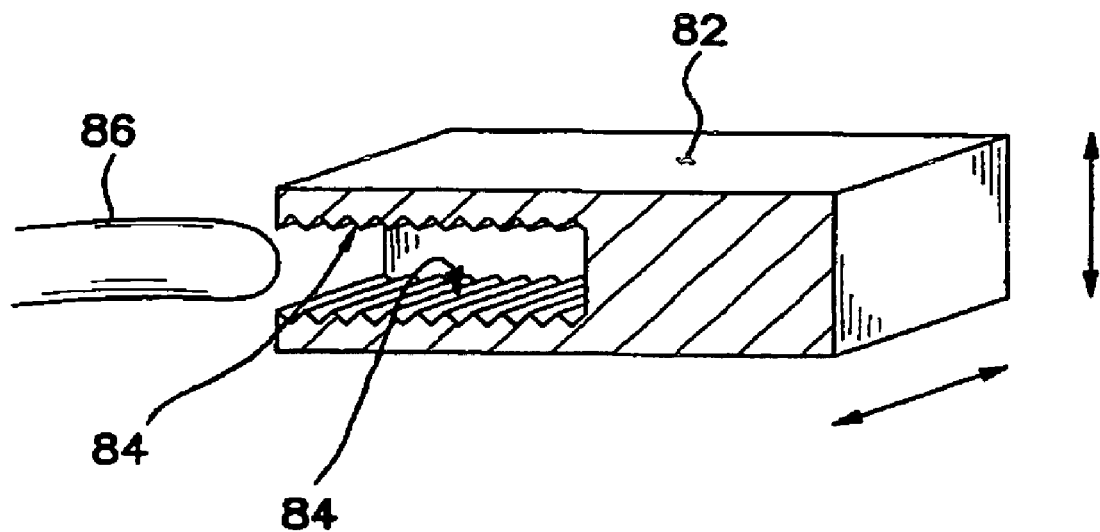
FIGS. 8A and 8B are schematic illustrations of tongue-treatment embodiments.
Figure 8B:
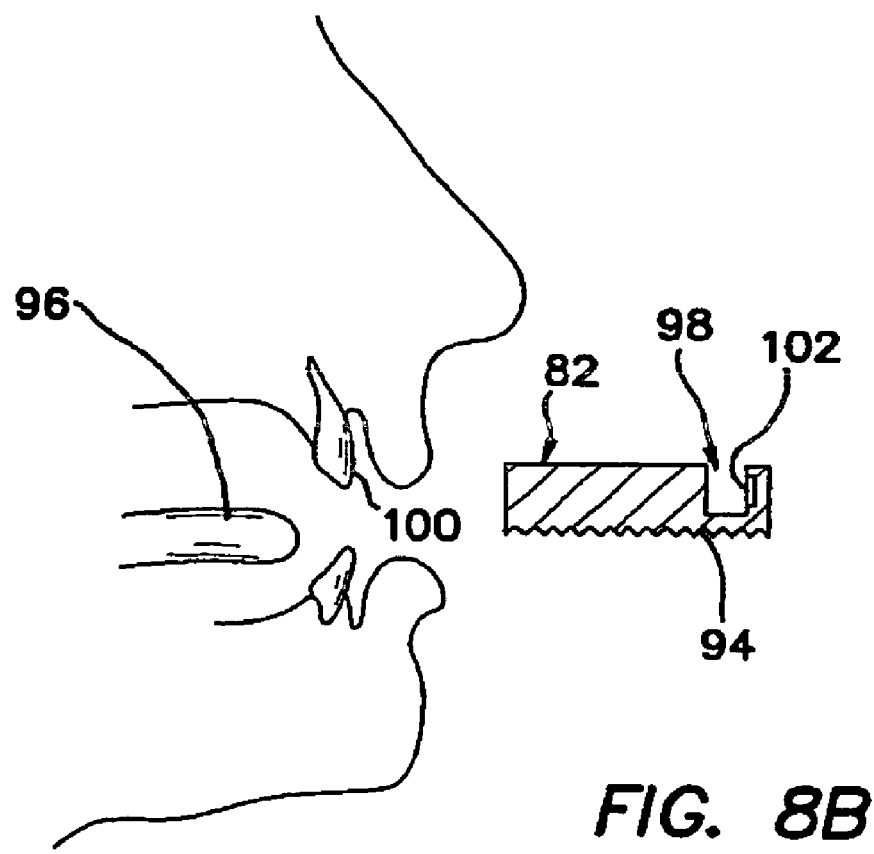

FIGS. 8A and 8B are schematic illustrations of tongue-treatment embodiments. In FIG. 8A, the tongue-treatment embodiment comprises a stand-alone tongue cleaner 82 having a shaped, brushed or otherwise textured surface 84 that may comprise various degrees of hardness. The surface or surfaces 84 operate at least in part to form a cavity or wrap for accommodating a tongue 86 of a patient and, further, operate to contact the tongue for cleaning thereof. The tongue cleaner 82 can comprise one or motion devices, such as oscillation or ultrasonic devices, for causing the tongue cleaner to move in one or more of the directions of the double-headed arrows shown in the figure. FIG. 8B shows tongue cleaner assembly 92 that is integrated with a mouth tray. As such, implementations of the device for treating oral tissue can be provided in a package. This tongue cleaner assembly 92 may comprise a shaped, bristled or otherwise textured surface 94 that may comprise various degrees of hardness. The surface 94 operates to contact a tongue 96 of a patient for cleaning thereof. The tongue cleaner assembly 92 comprises a cavity 98 for accommodating teeth 100 and a light source 102 within the cavity 98 for irradiating the teeth 100.

FIGS. 9-13D depict modified embodiments of carriers and related structures provided with activated (e.g., moving and light-emitting) textured surfaces for automatically cleaning (e.g., brushing) or whitening a user's teeth. Upon insertion and activation of the carrier, either at a home or in a clinic, a user's teeth can be treated (e.g., whitened and/or cleaned). The illustrated embodiments comprise vibrating carriers that treat (e.g., agitate and whiten) the user's teeth with little to no effort on the part of the user following insertion and activation of the carrier.

Interior wall surfaces of the vibrating carriers on which, for example, the textured surfaces can formed, as presently embodied, can comprise one or more of the above-mentioned electromagnetic radiation sources (e.g., optical fiber panels 42) for performing any of the functions described herein. The electromagnetic radiation sources may be externally powered and supplied and/or powered or supplied from one or more sources of electromagnetic radiation (e.g., light) or other power (e.g., batteries) within, for example, a driver region (e.g., a driver box, discussed below) of the vibrating carrier.

The activated textured surfaces influence (e.g., contact) tissues to be treated (e.g., teeth) of the user following insertion of the vibrating mouthpiece into the user's mouth and activation, to enable, for example, vibration of and light-emission from, the activated textured surfaces for facilitating treatment. In the illustrated embodiment, the activated textured surfaces are secured to or are formed with interior wall surfaces of the vibrating carriers in locations designed or intended to come into contact with or otherwise treat tissues (e.g., hard or soft) in need of treatment within the user's mouth upon insertion of the vibrating mouthpiece into the user's mouth.

According to the illustrated embodiments, the activated textured surfaces comprise bristles. Typical embodiments include bristles formed and secured to the interior wall surfaces using any of a variety of manufacturing techniques known to those skilled in the art. The interior wall surfaces can have bristles flush mounted and/or integrally formed into the interior wall surfaces to extend away from the interior wall surfaces of the vibrating mouthpiece using manufacturing techniques known to those skilled in the art. For example, the bristles can be over-molded into the interior wall surfaces of the vibrating mouthpiece. The bristles typically will be fabricated to extend normally from the interior wall surfaces as shown. In an illustrated embodiment, the vibrating mouthpiece can comprise at least one transparent wall (e.g., the interior wall surfaces for holding the bristles). The bristles may comprise transparent structures in one embodiment, and in typical embodiments the bristles have lengths shorter than (e.g., 25% as long as) those found on typical toothbrushes. According to an aspect, the dentifrice may be layered. A first layer of the dentifrice may comprise a first active ingredient; a second layer of the dentifrice may comprise a second active ingredient. The dentifrice can be arranged so that the second layer is positioned furthest away from the electromagnetic radiation source. The activated textured surface can comprise bristles of a first height and bristles of a second height greater than the first height. Bristles of a second height can be constructed to direct electromagnetic energy through a first layer of the dentifrice and into a second layer of the dentifrice. Furthermore, the bristles of the second height can be constructed to output a greater power. Also, distal ends of the bristles of the second height can extend at least partially through the first layer.

As illustrated in FIGS. 9-13D, the vibrating carrier can be provided in the form of a vibrating mouthpiece configured to fit over at least a portion of a person's teeth. For example, the vibrating carrier as shown can fit over a person's front upper and lower teeth for treatment (e.g., whitening) thereof. The vibrating carrier may be generic or custom designed, or may be moldable (e.g., bendable by way of upper and lower moving arms, which may comprise a bendable metal as known in the art). In typical embodiments, one vibrating carrier may fit over both the upper and lower teeth.

A perspective view of such a vibrating carrier in the form of a vibrating mouthpiece 103, which can be constructed to have any one or more of the structures and functionalities (e.g., emitting light) as described above, is shown in FIG. 9. It is noted that the embodiment shown can comprise a size to accommodate front teeth 105 of the user or to accommodate all or substantially all of the user's teeth, or just a top or bottom part of a row of either of the mentioned sets of teeth 105. Moreover, the vibrating mouthpiece 103 can be bent (e.g., by way of upper and lower moving arms comprising a bendable metal) to match the curvatures of a user's mouth and teeth.

Figure 9:
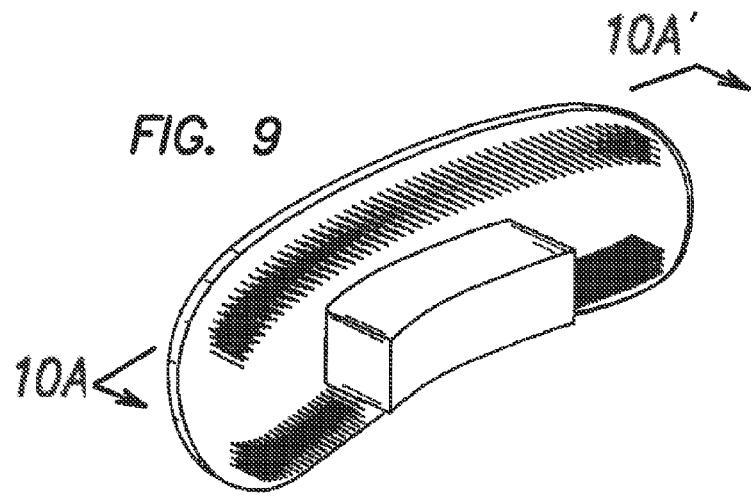
FIGS. 9-13D depict additional embodiments of the present invention.

The top, bottom, back and two sides of the pocket or housing 101 in FIG. 9 can all comprise solid walls. All five of these sides fit into the user's mouth, as do the bristles 107. The front side of this housing 101, on the other hand, facing into the page of the drawing or in a direction away from the direction of the bristles 107, is preferably open. While currently depicted with a rectangular shape, other shapes and sizes may be implemented as well.

Figure 10A:
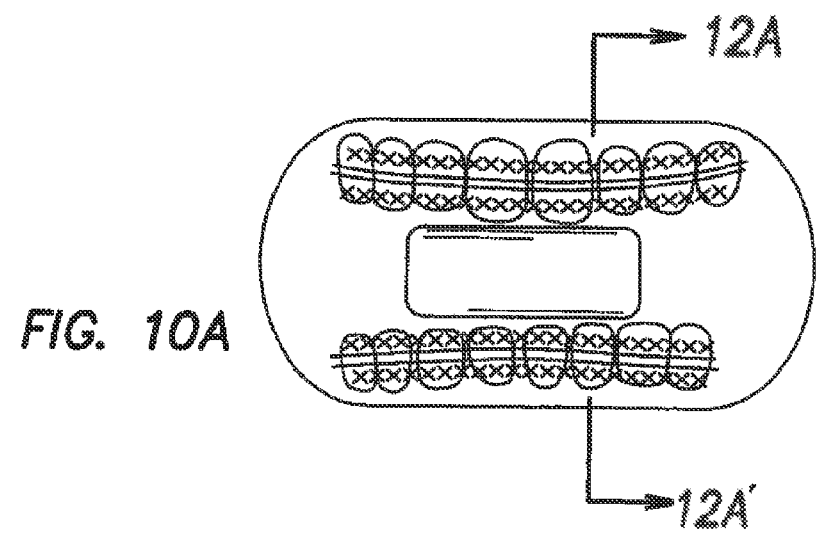
Figure 10B:
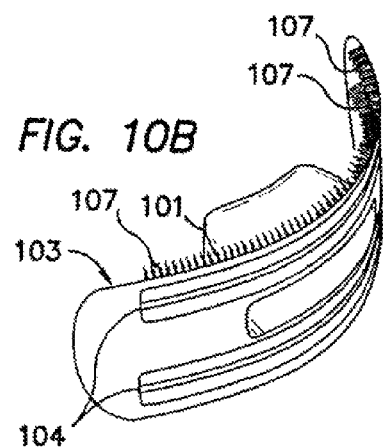

10A is a side-elevation view as taken from a direction of the line 10A-10A' of FIG. 9, and FIG. 10B is a perspective view of the same assembly. The views of the housing 101 in FIGS. 10A and 10B span through the open side of the housing 101 and to the solid back side of the housing 101. In other words, the view of FIG. 9 shows the back or closed side of the housing or pocket 101, and FIGS. 10A and 10B show the open side or opening of the housing or pocket 101. The teeth 105 and rows of bristles 107 shown in FIG. 10A would of course be located behind the shown front surface of the vibrating mouthpiece 103 (e.g., within the user's mouth). Also depicted in FIGS. 10A and 10B are upper and lower grooves 104. Since the upper and lower grooves 104 illustrated in FIGS. 10A and 10B are disposed within the front surface of the vibrating mouthpiece 103, they are viewable from the direction of the arrows 10-10' of FIG. 9.

Figure 11A:
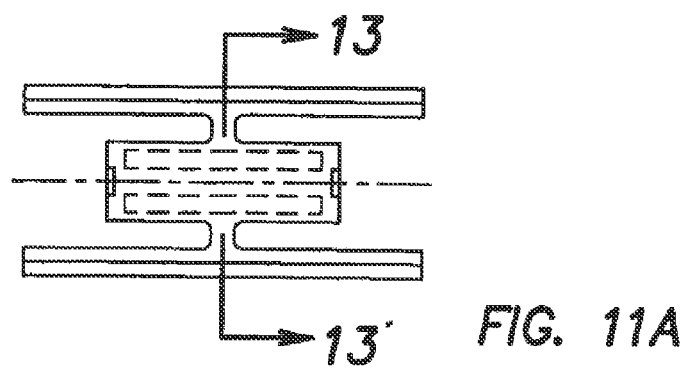
Figure 11B:
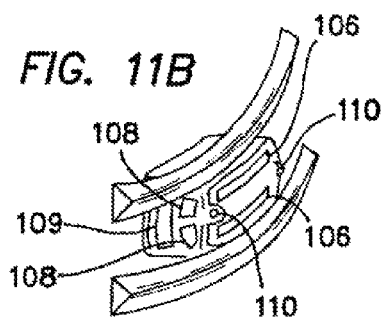

FIGS. 11A and 11B depict a front assembly and a driver region (e.g., box), which is discussed in more detail below. In FIG. 11A, the front assembly is oriented directly in front of the driver box so that the only part of the driver box that can be seen are two ears, discussed below, on left and right sides of the driver box. The front assembly comprises upper and lower moving arms. These upper and lower moving arms correspond (e.g., are complementarily shaped) to and fit into the upper and lower grooves 104 within the front surface of the vibrating mouthpiece 103. With regard to the front assembly, it can include, and is depicted in these two figures as comprising, for example, a generally planar and slightly-curved (e.g., arched) shape. An outer surface (e.g., the surface shown in FIG. 11A and shown to the right in FIGS. 13A and 13B) of the front assembly can further be formed integrally with, or removably connected to the upper and lower moving arms, which may be embodied as elongated structures as shown in the figures. The generally planar and slightly-curved member further may be formed to contain driven pads 106 (e.g., metal and/or magnetic), which communicate with driver pads 108, as discussed below.

The upper and lower moving arms can be powered by a motor or other motion imparting implement, to thereby provide mechanical forces to the corresponding upper and lower grooves 104, which motion, in turn, can be transferred to the bristles 107. In the illustrated embodiments, the motion imparting implement is powered by electromotive forces, such as inductive couplings and/or driver (e.g., magnetic) pads 108 for communicating with the driven pads 106. The driver pads 108 can be positioned within the housing 101 and supplied power by batteries 109 also positioned within the housing 101. The motion imparting implement can comprise the driver box and the front assembly (of which the upper and lower moving arms are a part).

As shown, the driver box fits into the housing 101 and also accommodates the front assembly (of which the upper and lower moving arms are a part). While depicted with a rectangular shape, other shapes and sizes of driver boxes may be implemented as well. Regarding the fitting of the driver box into the housing 101, the driver box may comprise, for example, top, bottom, left, right and back sides for contacting and resting against the corresponding top, bottom, left, right and back sides of the housing 101. As with the design of the housing 101, the front side of the driver box can be open. Regarding the accommodation by the driver box of the front assembly (containing the upper and lower moving arms), in the illustrated embodiment, left and right sides of the driver box can comprise a coupler which operates to position and hold the front assembly to the driver box.

According to certain illustrated embodiments, the coupler also can operate to allow the front assembly to move relative to the driver box. For example, the coupler can comprise structure for allowing the front assembly to rock or pivot and/or can comprise structure for allowing the front assembly to slide or move in a linear direction, relative to the driver box. In certain implementations, such as those shown in FIGS. 11A, 11B, 11C, 13A and 13D, the coupler can comprise ears having apertures 110 for forming an axis that allows the front assembly to pivot about the axis and/or, as exemplified in FIG. 13B, can comprise ears having slots 112 forming a track for movement of the front assembly along the track. Pivoting movement of the front assembly relative to the driver box may be effectuated by movement of one or more of the upper and lower moving arms, and, similarly, translation movement of the front assembly can be effectuated by corresponding movements of one or more of the upper and lower moving arms.

Figures 12A, 13A, 13B:
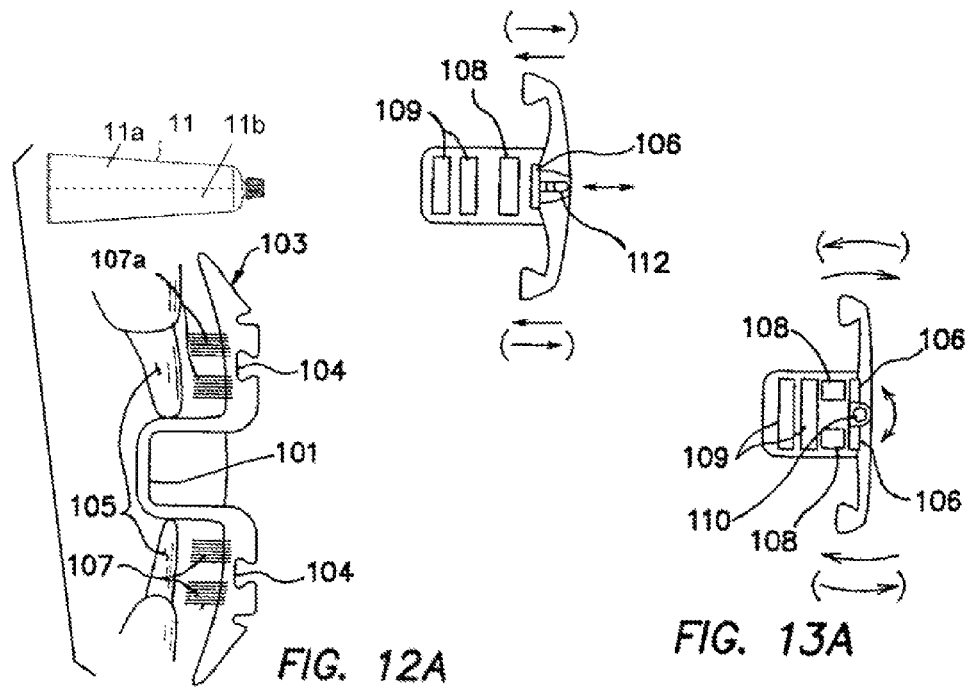

FIG. 12A shows a cross-sectional view of the bristle-containing portion of the vibrating mouthpiece 103 shown in FIG. 10A, wherein the cross-sectional view is taken along the line 12A-12A' of FIG. 10A. The view of FIG. 12A shows the housing 101, bristles 107, the front surface, and the upper and lower grooves 104. In one aspect, a dentifrice 11 may be provided of a first layer 11a comprising a first ingredient and a second layer 11b comprising a second ingredient with for instance the activated textured surface 107a comprising bristles of first and second heights. This view further shows a pair of flex joints (e.g., grooves) disposed above and below the upper and lower grooves 104. As depicted in FIG. 12A, upon insertion of the vibrating mouthpiece 103 into a user's mouth, the user can bite down on the upper and lower sides of the housing 101 to align his or her teeth with the bristles 107.

FIGS. 13A and 13B show cross-sectional views of the front assembly and driver box of FIG. 11A. The views of these figures are taken from a direction of the line 13-13' of FIG. 11A. In particular implementations of the present invention, the coupler may comprise a plurality of couplers. Regarding each coupler, which is typically formed as a part of the driver box, the coupler may comprise, for example, two or more ears as depicted in the group of FIGS. 11A, 11b, 13A and 13B. The ears of FIG. 13A, for example, may be formed as extensions of the left and right sides of the driver box, and, further, may comprise apertures for accommodating pins of the front assembly. The ears of FIG. 13B, for example, may be formed as extensions of the left and right sides of the driver box and may comprise apertures, recesses or tracks for accommodating pins or other extensions of the front assembly.

In other implementations, each of the ears of FIGS. 13A and 13B is formed to comprise one or more bumps or other protuberances for fitting around and contacting the outer surface of the front assembly, to thereby secure the front assembly to the driver box. The pins of the front assembly in these implementations can be optional. According to further implementations, each of the ears of FIGS. 13A and 13B can be formed to comprise one or more indentations, and the corresponding outer surfaces of the front assembly can be formed to have one or more complementarily-shaped protuberances or other suitable structures for fitting into the indentations, to thereby allow the front assembly to be secured to the driver box.

FIGS. 10C and 11C are side-elevation views taken from a direction of the line 10-10' of FIG. 9, according to an embodiment wherein bristles 107 are applied to teeth in addition to just the front top and front bottom teeth. More particularly, the structures of these figures, along with those of FIGS. 13C and 13D, are designed to apply bristles 107 to back surfaces of teeth, as well, and, accordingly, may be suitable for purposes in addition to or other than, for example, cosmetic (e.g., whitening) purposes. For example, such structures may be implemented to effectuate brushing of, for example, all of a user's gum lines. In such embodiments, the components used to drive the bristles 107 for treating outer surfaces of teeth as described above are duplicated to drive bristles 107 for treating inner surfaces of the teeth. Furthermore, in certain implementations of these embodiments, the housing 101 may be extended to one of the two edges of the vibrating mouthpiece 103 (e.g., extended to the right edge of the vibrating mouthpiece 103 as indicated in FIG. 10C wherein the two "x" marks indicate center areas of the vibrating mouthpiece), and the one open side of the housing 101 may be formed on the right side rather than on the back side of the housing 101, whereby the front assembly is then inserted through the open right side and slid into a center position (e.g., centered on the "x" marks).

The structures of FIG. 12B correspond to an oral-tray type of embodiment wherein additional bristles 107 are disposed on surfaces of the vibrating mouthpiece 103 to effectuate treatment (e.g., brushing) of grinding surfaces of the user's teeth. According to certain implementations, the parts of the vibrating mouthpiece 103 shown in FIGS. 10A, 10B and 10C can be disposable, and the parts shown in FIGS. 11A, 11B and 11C can be sterilizable and reusable.

In using the foregoing devices of the invention, a treatment implementation can be placed or formed on the bristles or in the oral tray. According to embodiments wherein the treatment implementation comprises a dentifrice, the tray with dentifrice applied thereto (e.g., placed in the tooth bed of the oral tray) can be fit over the upper or lower teeth, and an electromagnetic radiation source can then be activated while the tray is kept in the mouth for a predetermined duration. The dentifrice may typically contain one or more active ingredients depending on the particular application. As a few examples, the dentifrice may include one or more of the following compounds: peroxy compounds (such as, hydrogen peroxide and/or carbamide peroxide), oxidoreductase agents (such as laccases, oxidases, and/or peroxidases), antibacterial agents (such as chlorhexidine digluconate, hexetidine, alexidine, quarternary ammonium and water-soluble sources of certain metal ions such as zinc, copper, silver, and stannous), anti-carries agents (such as fluoride), anti-plaque agents or plaque control activators, anti-tartar agents, desensitizing agents, etching agents (such as phosphoric acid), photosensitizers and photodynamic therapy photosensitizers, whitening agents, or pigments. The dentifrice may additionally or alternatively be conditioned (e.g., flavored) and comprise, in whole or in part and in any combination with the preceding ingredients, any of the ingredients as described in U.S. Pat. No. 6,350,123, entitled FLUID CONDITIONING SYSTEM, the contents of which are incorporated herein by reference.

Figure 5:
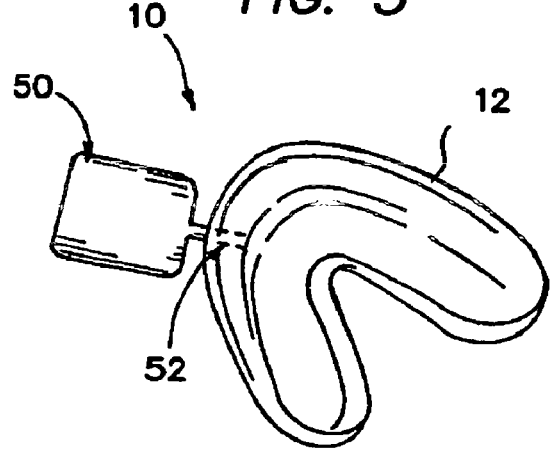
FIG. 5 is a perspective view of the device of the invention having a dentifrice cartridge connected to the device.
Figure 6:
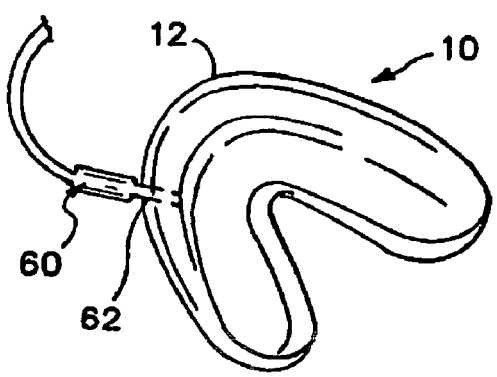
FIG. 6 is a perspective view of the device of the invention having an aspirator connected to the device.

The oral tray of the invention may also include one or more attachments to deliver, for example, a dentifrice from a cartridge 50 through a cartridge channel 52 directly into the tray (FIG. 5). The same attachment, or a different attachment, can be used, additionally or alternatively, for connecting an aspirator 60 to aspirate the dentifrice and/or other fluids through aspirator channel 62 from the oral tray in connection with the performance of a procedure (cf. FIG. 6).

In other particular embodiments of the invention, the oral trays may include separate compartments to be aligned with a subject's gum line. Such compartments may serve to contain an isolating gel that protects the gums from contact with the active ingredients of the dentifrice. The isolating gel may also include a thermal insulator that may help prevent heat transfer from the tray and/or the dentifrice to the gums. In addition, the oral tray may be structured to accept gel only on the side of the teeth requiring treatment, for example, the front side. The oral tray may include two or more sub-trays inside the main tray that provide selective treatment on different groups of teeth at the same time. For example, one sub-tray may be used for a fluoride treatment of the back molars, and another sub-tray may be used for whitening the front teeth. The compartments may, for example, permit selective procedures to be performed on desired regions of the teeth or mouth, and/or may help protect sensitive areas of the mouth. Thus, the device of the invention may include one or more compartments to customize the application of the device. The selective targeting of areas by the sub-trays, and/or by other means, may be based on or determined by, at least in part, information acquired from a detector or detectors as previously described.

The carrier (e.g., oral tray) may also be constructed to emit heat. This may be in addition to, or instead of, the electromagnetic radiation source. For example, a dry chemical heat-emitting material may be incorporated or added to the oral tray. The emission of heat may be activated after the user places the tray on his teeth and the user starts biting down on the tray. One example of a suitable chemical is sodium acetate trihydrate. In certain embodiments, the heat source is incorporated into the carrier so that the subject using the carrier does not ingest the heat source.

FIG. 7A depicts a carrier embodied as another oral device 10, which is formed as an oral band or oral tape 72 attached to a person's oral tissue (e.g., teeth). In modified embodiments, the oral device may comprise an oral band, tape or wrap applied on or around one or more of a tongue, gums and teeth of a user. In the illustrated embodiment, oral tape 72 comprises a plurality of intersecting lines. The cross-section along line 7B-7B is shown in FIG. 7B. Oral tape 72 can include an electromagnetic radiation source 20 and/or may also include one or more compartments 50 containing a dentifrice with an active ingredient sensitive, for example, to activation (via, e.g., one or more of a repetitive movement mechanism and an electromagnetic radiation source as described previously). In an illustrative embodiment, the activation is achieved with electromagnetic radiation. Each tooth of the subject may be covered by one or more of the compartments. A protective layer 74 may be provided over compartments 50 to prevent leakage of the dentifrice from the compartments. Protective layer 74 may be peeled off before applying the tape to the tissue (e.g., teeth). Alternatively, the protective layer may be made of a material subject to degradation by enzymes contained in a subject's mouth, where the enzymes dissolve the protective layer and thereby permit the dentifrice to be applied to the tissue. The electromagnetic radiation source may comprise a thin layer of woven optical fibers (e.g., Lumitrex), similar to that discussed above, a thin layer of LEDs, or even an organic or polymeric thin-film of luminescent material.

Examples of potential compounds or agents used in organic or polymeric thin-film luminescence include, but are not limited to, end-capped oligothiophenes, tris-chelated polypyridyl ruthenium (II) complexes, polyphenylenes, doped tris-8-(hydroxyquinoline) aluminum, indium tin oxides, polyfluorenes, vinylene-bridged triphenylamine dimers, rhodamine 6G, bicarbazyles, 1,1,4,4-tetraphenyl-1, 3-butadiene-doped polymeric Langmuir-Blodgett films, inorganic CdSe nanocrystals, carbazole-substituted polyacetylenes The electromagnetic radiation source may be powered by any suitable means that can cause electromagnetic radiation to be emitted from the source or sources. For example, the carrier electromagnetic radiation source may include one or more batteries, or an electrical power cord plugged into an electrical outlet. Batteries may be embedded in the carrier or may be disposed externally to the carrier. Oral tape, for example, may be provided with batteries placed within the tape and/or may be capable of being charged using a charging device.

In addition to being configured to control, for example, one or more of any characteristic or functionality of the electromagnetic radiation source, movement mechanism, electronic input/output device, and/or detector(s), the circuit and/or microprocessor may be programmable to further effectuate or optimize treatment protocols. For example, in a context of tooth-whitening, the programmable microprocessor may control parameters such as light, wavelength, brightness, power, or duration of emission, wherein such parameters may be programmed as presets, or may be operated manually by the user. The user may control the speed of whitening by selecting the wavelength, the brightness, the power, and the time of exposure. For in-office procedures, a clinician may decide the specific parameters suited for the patient. For out of office procedures, such as home use, the user may select one of the preset programs. As a particular example, a program may provide a higher light intensity for a relatively short duration. In addition, the oral device may include a sensor device that, through software control, informs the user when the process is completed or the treatment time has expired.

Thus, the oral device of the invention may be relatively easy to use, and may provide fast and effective treatment over conventional devices. The oral device of the invention may provide, for example, one or more of selective treatment for specific tissue (e.g., tooth) surfaces, better alignment, and a more controlled, uniform treatment. The device further may reduce tissue (e.g., tooth) sensitivity. In the context of tooth whitening, for example, the device may require less time for wearing the device, may provide means for treating teeth or a portion of teeth locally, and/or may reduce discomfort associated with whitening agents contacting the teeth for a relatively extended period of time.

The above-described embodiments have been provided by way of example, and the present invention is not limited to these examples. Multiple variations and modification to the disclosed embodiments will occur, to the extent not mutually exclusive, to those skilled in the art upon consideration of the foregoing description. Additionally, other combinations, omissions, substitutions and modifications will be apparent to the skilled artisan in view of the disclosure herein. Accordingly, it is intended that the present invention not be limited by the disclosed embodiments, but be defined by reference to any appended additional disclosure in claims format.

The invention claimed is:

1. A device for treating oral tissue, comprising:
a carrier constructed to be applied in proximity to at least one oral tissue within a mouth;
an activated textured surface coupled to the carrier and comprising first and second sets of members constructed for being activated and moved in different ways thereby to impart different repetitive movements to the first and second sets of members and further to impart electromagnetic radiation, from at least a first electromagnetic radiation source and a second electromagnetic radiation source having a different wavelength, to the oral tissue; and
a dentifrice disposed on the activated textured surface, the dentifrice having a first layer with a first active ingredient that is more sensitive to wavelengths from the first electromagnetic radiation source and a second active layer with a second ingredient that is more sensitive to wavelengths from the second electromagnetic radiation source;
wherein the activated textured surface comprises (a) bristles of a first height and (b) bristles of a second greater height constructed to direct electromagnetic energy through the first layer and into the second layer; and
wherein the device is a mouthtray and the activated textured surface comprises textured surfaces that are configured to be activated to automatically provide one or more of mechanical agitation and mechanical cleaning forces onto the oral tissue.

2. The device for treating oral tissue as set forth in claim 1, wherein:
the device has an upper portion and a lower portion;
the first and second sets of members are coupled, respectively, to the upper portion and lower portion; and
the activated textured surface comprises bristles.

3. The device for treating oral tissue as set forth in claim 2, wherein:
the different ways of movement of the first and second sets of members comprise arcuate paths; and
the device comprises an element for imparting movement forces to the bristles.

4. The device for treating oral tissue as set forth in claim 3, wherein the activated textured surface is constructed to apply repetitive bristle movements onto surfaces of the oral tissue to thereby impart a cleaning effect to the oral tissue.

5. The device for treating oral tissue as set forth in claim 4, wherein the activated textured surface is constructed to apply repetitive bristle movements onto surfaces of teeth.

6. The device for treating oral tissue as set forth in claim 5, wherein:
the device is provided in a package; and
the device further comprises a dentifrice disposed on at least a portion of the bristles.

7. The device for treating oral tissue as set forth in claim 6, wherein the activated textured surface is constructed to apply repetitive bristle movements onto parts of the oral tissue simultaneously with the imparting of electromagnetic radiation from the device to the parts of the oral tissue.

8. The device for treating oral tissue as set forth in claim 7, wherein:
the activated textured surface is constructed to apply repetitive bristle movements onto the parts of the oral tissue by operation of a motor; and
the activated textured surface is further constructed to impart electromagnetic radiation to the parts of the oral tissue by operation of an electromagnetic radiation source.

9. The device for treating oral tissue as set forth in claim 6, wherein the dentifrice is spray or dip coated on the bristles.

10. The device for treating oral tissue as set forth in claim 6, wherein the bristles comprise hollow portions that contain the dentifrice.

11. The device for treating oral tissue as set forth in claim 6, wherein the dentifrice is at least partially surrounded by and held between longitudinal outer surfaces of groups of bristles.

12. The device for treating oral tissue as set forth in claim 1, wherein:
the device is provided in a package; and
the device comprises a dentifrice disposed on the activated textured surface.

13. The device for treating oral tissue as set forth in claim 12, wherein the dentifrice is spray or dip coated on the activated textured surface.

14. The device for treating oral tissue as set forth in claim 12, wherein the activated textured surface comprises hollow or concave portions which contain the dentifrice.

15. The device for treating oral tissue as set forth in claim 12, wherein the dentifrice is at least partially surrounded by and held between protuberances of the activated textured surface.

16. The device for treating oral tissue as set forth in claim 1, wherein:
    the activated textured surface is constructed to apply repetitive cleaning forces onto parts of the oral tissue by operation of a motor; and
    the activated textured surface is further constructed to impart electromagnetic radiation to the parts of the oral tissue by operation of at least one electromagnetic radiation source.

17. The device for treating oral tissue as set forth in claim 1, wherein the activated textured surface comprises bristles.

18. The device for treating oral tissue as set forth in claim 12, wherein the device is a mouthtray.

19. The device for treating oral tissue as set forth in claim 12, wherein:
    the activated textured surface is constructed to apply repetitive cleaning forces onto parts of the oral tissue by operation of a motor and to impart electromagnetic radiation to the parts of the oral tissue by operation of at least one electromagnetic radiation source; and
    the electromagnetic radiation source comprises a plurality of light emitting diodes (LEDs).

20. The device for treating oral tissue as set forth in claim 1, further comprising a plurality of sensors enabling an identification of at least one treatment condition of the oral tissue and an automatic notification to a user of the condition.

21. The device for treating oral tissue as set forth in claim 20, wherein:
    the sensors collect one or more of gases and light from the oral tissue to identify the at least one treatment conditions; and
    the device is configured to notify the user of treatment conditions comprising one or more of periodontal disease, halitosis, bronchitis, and a tumorous growth.

22. The device for treating oral tissue as set forth in claim 1, and further comprising cartridge or aspirator.

23. The device for treating oral tissue as set forth in claim 1, wherein the dentifrice is arranged so that the second layer is positioned furthest away from the electromagnetic radiation sources.

24. The device for treating oral tissue as set forth in claim 1, wherein the bristles of the second height are constructed to output a greater power.

25. The device for treating oral tissue as set forth in claim 1, wherein distal ends of the bristles of the second height extend at least partially through the first layer.

* * * * *